US008318435B2

(12) United States Patent
Aikawa et al.

(10) Patent No.: US 8,318,435 B2
(45) Date of Patent: Nov. 27, 2012

(54) **DNA EXTRACTION METHOD FOR *BURSAPHELENCHUS XYLOPHILUS* FROM WOOD CHIPS, LAMP PRIMER SET FOR *BURSAPHELENCHUS XYLOPHILUS*, AND DETECTION METHOD FOR *BURSAPHELENCHUS XYLOPHILUS* FROM WOOD CHIPS**

(75) Inventors: Takuya Aikawa, Ibaraki (JP); Taisei Kikuchi, Ibaraki (JP); Natsumi Kanzaki, Ibaraki (JP)

(73) Assignee: Forestry and Forest Products Research Institute, Ibaraki (JP)

( * ) Notice: Subject to any disclaimer, the term of this patent is extended or adjusted under 35 U.S.C. 154(b) by 118 days.

(21) Appl. No.: 12/989,870

(22) PCT Filed: Oct. 23, 2008

(86) PCT No.: PCT/JP2008/069185

§ 371 (c)(1), (2), (4) Date: Nov. 24, 2010

(87) PCT Pub. No.: WO2009/136456

PCT Pub. Date: Nov. 12, 2009

(65) Prior Publication Data

US 2011/0159503 A1 Jun. 30, 2011

(30) Foreign Application Priority Data

May 7, 2008 (JP) ................................ 2008-121316

(51) Int. Cl.
*C12Q 1/68* (2006.01)
*C12P 19/34* (2006.01)
*C07H 21/04* (2006.01)

(52) U.S. Cl. ...... 435/6.12; 435/6.1; 435/6.11; 536/24.3; 536/24.33

(58) Field of Classification Search ........................ None
See application file for complete search history.

(56) References Cited

FOREIGN PATENT DOCUMENTS

| | | |
|---|---|---|
| CN | 1614396 | 12/2004 |
| CN | 1793866 | 12/2005 |

OTHER PUBLICATIONS

International Preliminary Report on Patentability and English translation of the Written Opinion issued Dec. 23, 2010 in International (PCT) Application No. PCT/JP2008/069185.
C. Francois et al., "Satellite DNA as a target for TaqMan real-time PCR detection of the pinewood nematode, *Bursaphelenchus xylophilus*", Molecular Plant Pathology, 2007, 8(6), pp. 803-809.
Y. Takeuchi et al., "A nested PCR-based method for detecting the pine wood nematode, *Bursaphelenchus xylophilus*, from pine wood", Nematology, 2005, vol. 7(5), pp. 775-782.
H. Iwahori et al., "PCR-RFLP and sequencing analysis of ribosomal DNA of *Bursaphelenchus* nematodes related to pine wilt disease", Fundam. appl. Nematol., 1998, 21(6), pp. 655-666.
Y. Liu et al., "Establishment of Standard Positive Control and PCR Detection System for *Bursaphelenchus xylophilus*", Chin. J. Appl. Environ. Biol., vol. 14, No. 1, pp. 122-125, Feb. 2008. Abstract Only.
M. Wang et al., Studies on Real-Time Fluorescent PCR with TaqMan Probe for rDNA — ITS2 of Pine Wood Nematode (*Bursaphelenchus xylophilus*), Linye Kexue, vol. 41, No. 2, pp. 82-85, 2005. Abstract Only.
International Search Report issued Jan. 13, 2009 in International (PCT) Application No. PCT/JP2008/069185.
N. Kanzaki et al., "Nested PCR-ho o Mochiita Kuromatsuzai kara no. Matsuzai Senchu Kenshutsu", The Japanese Forest Society Taikai Koen Yoshishu, vol. $116^{th}$, PA168, 2005.
Y. Liu et al., "Establishment of Standard Positive Control and PCR Detection System for *Bursaphelenchus xylophilus*", Chin. J. Appl. Environ. Biol., vol. 14, No. 1, pp. 122-125, Feb. 2008.
A. X. Cao et al., "Detection of the Pinewood Nematode, *Bursaphelenchus xylophilus*, using a Real-Time Polymerase Chain Reaction Assay", Phytopathology, vol. 95, No. 5, pp. 566-571, 2005.
T. Aikawa et al., "Demonstration of Interbreeding between Virulent and Avirulent populations of *Bursaphelenchus xylophilus* (Nematoda: Aphelenchoididae) by PCR-RFLP Method", App. Entomol. Zool., vol. 38, No. 4, pp. 565-569, 2003.
M. Wang et al., Studies on Real-Time Fluorescent Pcr with TaqMan Probe for rDNA — ITS2 of Pine Wood Nematode (*Bursaphelenchus xylophilus*), Linye Kexue, vol. 41, No. 2, pp. 82-85, 2005.
K. Nagamine et al., "Accelerated Reaction by Loop-Mediated Isothermal Amplification Using Loop Primers", Molecular and Cellular Probes, vol. 16, pp. 223-229, 2002.
H. Iwahori et al., "*Bursaphelenchus xylophilus* 18S Ribosomal RNA Gene, Partial Sequence", GenBank Accession No. U92464, Feb. 10, 1999.
H. Iwahori et al., "*Bursaphelenchus mucronatus*, 18S Ribosomal Rna Gene, Partial Sequence", GenBank Accession No. U93554, Apr. 15, 1997.
S. Donn et al., "DNA Extraction from Soil Nematodes for Multi-Sample Community Studies", Applied Soil Ecology, vol. 38, No. 1, pp. 20-26, Jan. 2008.

*Primary Examiner* — Young J Kim
(74) *Attorney, Agent, or Firm* — Wenderoth, Lind & Ponack, L.L.P.

(57) ABSTRACT

To extract and detect *Bursaphelenchus xylophilus* DNA without isolating *Bursaphelenchus xylophilus* from a piece of wood taken from a tree belonging to the genus *Pinus* and the like, provided are a method for extracting *Bursaphelenchus xylophilus* DNA from a collected piece of wood that includes *Bursaphelenchus xylophilus*, a LAMP primer set including primers that anneal to a specific region of *Bursaphelenchus xylophilus* DNA, and a method for detecting *Bursaphelenchus xylophilus* from a piece of wood by amplifying a DNA by a LAMP method using this primer set.

6 Claims, No Drawings

DNA EXTRACTION METHOD FOR *BURSAPHELENCHUS XYLOPHILUS* FROM WOOD CHIPS, LAMP PRIMER SET FOR *BURSAPHELENCHUS XYLOPHILUS*, AND DETECTION METHOD FOR *BURSAPHELENCHUS XYLOPHILUS* FROM WOOD CHIPS

This application is a U.S. national stage of International Application No. PCT/JP2008/069185 filed Oct. 23, 2008.

TECHNICAL FIELD

The present invention relates to a method for extracting *Bursaphelenchus xylophilus* DNA from a piece of wood that includes *Bursaphelenchus xylophilus*, a LAMP primer set comprising a primer that anneals to a specific region of *Bursaphelenchus xylophilus* DNA, a method for detecting *Bursaphelenchus xylophilus* from a piece of wood, and a method for detecting *Bursaphelenchus xylophilus* using gene amplification.

BACKGROUND ART

*Bursaphelenchus xylophilus* is a pine wilt disease pathogen that causes the most serious damage to forests in Japan. *Bursaphelenchus xylophilus* is an invasive species from North America that has caused dramatic damage to Japanese pines, which lacked resistance to *Bursaphelenchus xylophilus*. Currently, except for Hokkaido and Aomori prefectures, *Bursaphelenchus xylophilus* has spread throughout Japan.

To diagnose pine wilt disease, it is necessary to detect *Bursaphelenchus xylophilus* from a piece of wood taken from a dead pine tree. Conventionally, this is usually carried out by isolating *Bursaphelenchus xylophilus* from the piece of wood using the Baermann method and performing a morphological observation. The Baermann method (for example, refer to Non-Patent Document 1) is a method in which a specimen is wrapped in tissue paper and dipped in a funnel filled with water. If a nematode is in the specimen, the nematode will fall to the bottom of the funnel. The morphology of the fallen nematode can then be confirmed with a microscope to determine whether it is *Bursaphelenchus xylophilus* or not.

However, in addition to requiring a very long time for the isolation of the nematode from the piece of wood, the Baermann method requires specialist knowledge concerning nematode morphology. Furthermore, expensive equipment such as a microscope is necessary for detection of the nematode. Therefore, detection of *Bursaphelenchus xylophilus* has until now been carried out at specialist institutions having the people and equipment capable of distinguishing nematodes. In other words, an easy method for detecting *Bursaphelenchus xylophilus* has not existed until now.

[Non-Patent Document 1] Masahara Mamiya, Kazuyoshi Futai, Hajime Kosaka, Natsumi Kanzaki (2004), Wood Nematodes (Nematode Experiment Methods, edited by the Japanese Nematological Society, Japanese Nematological Society, Ibaraki) 134-153.

DISCLOSURE OF THE INVENTION

Problems to be Solved by the Invention

In fields such as food and medicine, detection methods for pathogens using DNA amplification have been proposed. However, as described below, since *Bursaphelenchus xylophilus* is present in trees, there is the special circumstance that the conventional methods employed in other fields cannot be practically applied.

The present invention was devised in view of such circumstances. It is an object of the present invention to provide a method for simple extraction of *Bursaphelenchus xylophilus* DNA from a piece of wood that includes *Bursaphelenchus xylophilus*, a *Bursaphelenchus xylophilus* LAMP primer set, and a *Bursaphelenchus xylophilus* detection method capable of easily detecting *Bursaphelenchus xylophilus* using gene amplification.

Means for Solving the Problems

Specifically, the present invention provides a method for extracting *Bursaphelenchus xylophilus* DNA from a piece of wood, comprising: dipping a piece of wood including *Bursaphelenchus xylophilus* in a solution including an enzyme which breaks down keratin; and extracting *Bursaphelenchus xylophilus* DNA.

Furthermore, the present invention provides a LAMP primer set, comprising primers for respective base sequences F3, B3, FIP, and BIP, which can be annealed to a specific region in a ribosome RNA gene (rDNA) of *Bursaphelenchus xylophilus* and which are represented by sequence ID Nos. 1 to 4 in a sequence listing (this primer set will be referred to in the present specification as “first primer set”). The LAMP primer set according to the present invention may also include a base sequence Loop-F primer represented by sequence ID No. 5 in a sequence listing (this primer set further including a Loop-F primer in addition to the base sequence F3, B3, FIP, and BIP primers will be referred to in the present specification as “second primer set”). These primer sets can be used for amplification of *Bursaphelenchus xylophilus* DNA extracted by allowing an enzyme which breaks down keratin to act on a piece of wood including *Bursaphelenchus xylophilus*.

In addition, the present invention provides a method for detecting *Bursaphelenchus xylophilus*, comprising: a step of dipping a piece of wood including *Bursaphelenchus xylophilus* in a solution including an enzyme which breaks down keratin and extracting *Bursaphelenchus xylophilus* DNA; and a step of amplifying and detecting the extracted *Bursaphelenchus xylophilus* DNA. The step of amplifying and detecting *Bursaphelenchus xylophilus* DNA can be carried out by amplifying and detecting a specific region of *Bursaphelenchus xylophilus* rDNA by a LAMP method using the first LAMP primer set or the second LAMP primer set.

Still further, the present invention provides a method for detecting *Bursaphelenchus xylophilus* DNA, characterized by including a step of amplifying and detecting a specific region of *Bursaphelenchus xylophilus* rDNA by a LAMP method using the first LAMP primer set or the second LAMP primer set.

Advantages of the Invention

According to the present invention, since *Bursaphelenchus xylophilus* DNA is extracted from a piece of wood while the *Bursaphelenchus xylophilus* is still in the piece of wood, the *Bursaphelenchus xylophilus* DNA can be extracted without isolating *Bursaphelenchus xylophilus* from the piece of wood. As a result, detection of *Bursaphelenchus xylophilus* using DNA can be realized.

Furthermore, according to the present invention, detection can be carried out by amplifying a specific region of *Bursaphelenchus xylophilus* rDNA by a LAMP method. Consequently, gene amplification and detection of *Bursaphelenchus xylophilus* can be carried out more accurately and easily, and at a lower cost.

DETAILED DESCRIPTION OF THE EMBODIMENTS

In the *Bursaphelenchus xylophilus* detection method according to the present embodiment, for example, by dipping a piece of wood taken from a tree belonging to the genus *Pinus* in a solution including an enzyme which breaks down keratin, and extracting the DNA, of the *Bursaphelenchus xylophilus* present in the piece of wood, the DNA is extracted without isolating the *Bursaphelenchus xylophilus* from the piece of wood. Next, detection of *Bursaphelenchus xylophilus* from the collected piece of wood is carried out by amplifying and detecting *Bursaphelenchus xylophilus* DNA by the LAMP method, which is a gene amplification method, using a primer set for the LAMP method that includes a primer which can specifically anneal to a specific region of *Bursaphelenchus xylophilus* rDNA.

Thus, conventionally, *Bursaphelenchus xylophilus* identification was carried out by isolating *Bursaphelenchus xylophilus* from a piece of wood by the Baermann method, and then performing a morphological observation using a microscope. In contrast, the present inventor first conceived of performing *Bursaphelenchus xylophilus* detection using DNA detection.

However, if a conventional DNA extraction method is applied to apiece of wood in which *Bursaphelenchus xylophilus* is present, it is difficult to efficiently extract the *Bursaphelenchus xylophilus* DNA from the piece of wood, and the extraction takes a great deal of time. On the other hand, while the DNA could be extracted and purified by crushing the piece of wood in which *Bursaphelenchus xylophilus* is present, such a method would require specialized equipment such as a crusher for crushing the piece of wood. Therefore, in situations where such specialized equipment is lacking, it is difficult to apply this method. In other words, in situations where such specialized equipment is lacking, *Bursaphelenchus xylophilus* has to be isolated from the piece of wood to extract the DNA, so that about the same amount of effort and time is required as for the Baermann method. Further, even if the above-described method could be applied, the extraction solution includes a large amount of components derived from the piece of wood, such as lignin. Therefore, in order to use DNA amplification for detection, the extracted DNA must be sufficiently purified.

Accordingly, the present inventor focused on keratin, which is one of the main components of the body surface of *Bursaphelenchus xylophilus*. As a result of diligent research, the present inventor discovered that by allowing an enzyme which breaks down the keratin to act on a piece of wood including *Bursaphelenchus xylophilus*, and dissolving the body surface of *Bursaphelenchus xylophilus*, the *Bursaphelenchus xylophilus* DNA in the resultant solution could be extracted, thereby completing the present invention. More specifically, according to the present invention, *Bursaphelenchus xylophilus* DNA can be extracted in a short period of time even if processes such as crushing the collected piece of wood are omitted or simplified. Furthermore, since there are few components derived from the piece of wood which seep into the DNA extraction buffer, the DNA purification step can also be omitted or simplified.

Furthermore, as a new gene amplification method, the LAMP (Loop-Mediated Isothermal Amplification) method developed by Eiken Chemical Co., Ltd., (Tochigi) is known. The LAMP method has high specificity and amplification efficiency, and allows for visual determination of amplification by the addition of a fluorescent pigment to the reaction system. Consequently, the LAMP method enables gene amplification and detection in a short period of time. In addition, since the LAMP method is an isothermal nucleic acid amplification method, a special temperature control device is unnecessary. Moreover, the strand displacement DNA polymerase used in the LAMP method does not need to have heat resistance, unlike in the PCR method. Consequently, compared with the PCR method, the reaction can be carried out at a lower cost. Therefore, if the LAMP method can be used to perform detection based on the genes of *Bursaphelenchus xylophilus, Bursaphelenchus xylophilus* gene amplification and detection can be carried out more easily and at a lower cost. As a result of diligent research, the present inventor discovered a primer (LAMP primer) set for the LAMP method, which can be specifically annealed to a specific region of *Bursaphelenchus xylophilus* rDNA, and which is represented by a sequence ID Nos. 1 to 4 in a sequence listing, thereby enabling detection based on the genes of *Bursaphelenchus xylophilus* using the LAMP method. In addition, by using a Loop-F primer represented by sequence ID No. 5 in a sequence listing, amplification and detection can be carried out in a shorter period of time.

A preferred embodiment according to the present invention will now be described in more detail.

First, the preparation of a *Bursaphelenchus xylophilus* DNA extraction solution obtained by extracting *Bursaphelenchus xylophilus* DNA from a piece of wood (pine specimen) in which *Bursaphelenchus xylophilus* is present will be described in detail. In the present embodiment, a collected pine specimen is placed in a solution (buffer solution, DNA extraction buffer) including an enzyme (hereinafter, "keratinolytic enzyme") which breaks down keratin, and incubated. Thereby, the DNA of the *Bursaphelenchus xylophilus* present in the pine specimen is extracted. The solution including the extracted DNA used as a DNA extraction solution. As the buffer solution, any buffer solution that can be used for DNA extraction may be used, as long as it has a keratinolytic enzyme activity. Examples include a buffer solution containing NaCl, tris-HCl, and EDTA. In this case, the NaCl may be from 100 to 150 mM, the tris-HCL from 10 to 50 mM, and the EDTA from 0.1 to 1 mM.

The keratinolytic enzyme according to the present embodiment is not especially limited. For example, Proteinase K (E.C.3.4.21.64) may be used. The keratinolytic enzyme dissolves cells and causes the DNA in the nucleus to elute into the DNA extraction buffer by breaking down keratin, which is one of the main components of the body surface of the *Bursaphelenchus xylophilus* in the pine specimen. Consequently, the *Bursaphelenchus xylophilus* DNA can be extracted directly from the pine specimen without isolating the *Bursaphelenchus xylophilus* from the piece of wood. Although the keratinolytic enzyme content in the DNA extraction buffer is not especially limited, the content can be set so that, for example, about 7.5 U/μL of keratinolytic enzyme is included in the extraction buffer. When preparing the DNA extraction solution, a DNA extraction kit including the keratinolytic enzyme may also be utilized by adding it to the DNA extraction buffer. An example of a DNA extraction kit that can be used is "ISOHAIR" (Nippon Gene Co., Ltd.).

The size of the piece of wood subjected to above-described extraction of *Bursaphelenchus xylophilus* DNA and the collection method do not limit the present invention, and may be set arbitrarily. Further, the type of tree from which the piece of wood is collected is not especially limited. Examples thereof include trees from the genus *Pinus*, such as the Japanese black pine, the Japanese red pine, the Ryukyu island pine, the Korean pine, the Japanese white pine, the Scots pine, the European black pine, the maritime pine, the mugo pine, the Monterey pine, the ponderosa pine, the western white pine, the Taiwan black pine, the Chinese black pine, the Himalayan white pine, the slash pine, the pitch pine, the lodgepole pine, the eastern white pine, the loblolly pine, the longleaf pine, the jack pine, the Table Mountain pine, the lacebark pine, and the Taiwan red pine. Furthermore, the above-described DNA extraction solution may also be subjected to known DNA purification processing and then amplification by the below-described LAMP method. In addition, the method for extracting DNA using a keratinolytic enzyme is not limited to only *Bursaphelenchus xylophilus* present in the piece of wood. Obviously, the DNA can also be extracted by making an enzyme act on the *Bursaphelenchus xylophilus* itself.

Next, the design of the LAMP primer according to the present invention will be described in detail. In the present embodiment, a LAMP method primer specific to *Bursaphelenchus xylophilus* was designed using a primer design support software on the basis of a determined base sequence of an ITS (internal transcribed spacer) region of the base rDNA of *Bursaphelenchus xylophilus*. More specifically, first, an rDNA ITS region of *Bursaphelenchus xylophilus* and that of Bursaphelenchus mucronatus (the most closely related species to *Bursaphelenchus xylophilus*) were amplified by the PCR method, and the base sequences of those regions were determined using an ABI3100 DNA sequencer (Applied Biosystems). The base sequence information for both species was analyzed using a LAMP primer design support software (Primer Explorer V4) provided on a web site of Eiken Chemical Co., Ltd. The LAMP primer was designed so that only *Bursaphelenchus xylophilus* DNA would be amplified.

The LAMP primer according to the present embodiment is designed as follows. Three regions, F3c, F2c, and F1c, from the 3' terminal side for a target gene in the rDNA ITS region is defined. Also, the regions B1, B2, and B3 toward the 5' terminal side for the target gene is defined. Four kinds of primer, F3, B3, FIP, and BIP, are designed for these six regions. Here, the complementary regions for the respective regions F3c, F2c, and F1c are F3, F2, and F1, respectively, and the complementary regions for the respective regions B1, B2, and B3 are B1c, B2c, and B3c, respectively.

Specifically, the F3 primer represented by sequence ID No. 1 is designed so that it has the F3 region, which is the complementary sequence to the F3c region.

Further, the B3 primer represented by sequence ID No. 2 is designed so that it has the B3 region, which is the complementary sequence to the B3c region.

In addition, the FIP primer represented by sequence ID No. 3 is designed so that it has the F2 region, which is the complementary sequence to the F2c region defined in the rDNA ITS region, on the 3' terminal side, and the same sequence as the F1c region on the 5' terminal side.

Still further, the BIP primer represented by sequence ID No. 4 is designed so that it has the B2 region, which is the complementary sequence to the B2c region, on the 3' terminal side, and the same sequence as the B1c region on the 5' terminal side.

In addition, the present embodiment includes a Loop-F primer represented by sequence ID No. 5. This enables the number of DNA synthesis origin during the amplification operation to be increased and the amplification reaction to be accelerated, which in turn allows the amplification and detection of *Bursaphelenchus xylophilus* DNA to be carried out in a shorter period of time. The Loop-F primer represented by sequence ID No. 5 is designed so as to have a complementary sequence to the region between the F1 region and the F2 region.

Next, the amplification operation carried out by the LAMP method using the above-described primer set on extracted DNA will be described.

The amplification operation carried out by the LAMP method can be performed as follows, for example. First, the reagents (for example, Bst DNA polymerase, a reaction buffer (reaction mix), the primer set, and distilled water) are mixed to prepare an amplification reaction solution. Here, the below-described fluorescence detection reagent may also be mixed in this amplification reaction solution.

For example, Loopamp (registered trademark; hereinafter the same) DNA amplification reagent kit sold by Eiken Chemical Co., Ltd can be used as the reaction reagents excluding the primer set. The Loopamp DNA amplification reagent kit includes the following components. 2× reaction buffer (2× reaction mix): 40 mM tris-HCl (pH 8.8), 20 mM KCl, 16 mM $MgSO_4$, 20 mM $(NH_4)_2SO_4$, 0.2% Tween 20, 1.6 M betaine, respective final concentrations of 2.8 mM in dATP, dCTP, dGTP, and dTTP; Bst DNA Polymerase 8 units/μL. Furthermore, for example, loopamp fluorescence detection reagent sold by Eiken Chemical Co., Ltd may be used as the below-described fluorescence detection reagent.

Next, the above-described *Bursaphelenchus xylophilus* DNA extraction solution is added to this amplification reaction solution, and the resultant mixture is incubated at 63° C., for example.

The LAMP method reaction is carried out on the basis of steps such as the following. (1) The FIP primer with sequence ID No. 3 anneals to template DNA. (2) A DNA strand that is complementary to the template DNA is synthesized starting from the 3' terminal of the F2 region of the FIP primer by the activity of the Bst DNA Polymerase. (3) The F3 primer with sequence ID No. 1 anneals to the outside of the FIP primer, and starting from the 3' terminal, DNA synthesis is extended while the DNA strand is released from the already-synthesized FIP primer by the activity of the Bst DNA Polymerase. (4) The DNA strand synthesized from the F3 primer and the template DNA form a double strand. (5) On the other hand, the DNA strand from the FIP primer, from which the DNA strand from the F3 primer was released, forms single strand DNA. This DNA strand has the regions F1c and F1, which are complementary to each other, at the 5' terminal side, and thus self-anneals to form a loop. (6) The BIP primer with sequence ID No. 4 anneals to the DNA strand that formed into a loop in the above step (5). Starting from the 3' terminal of this BIP primer, complementary DNA is synthesized. The loop formed in step (5) is released and extends. In addition, the B3 primer with sequence ID No. 2 anneals to the outside of the BIP primer. Starting from the 3' terminal of the B3 primer, DNA synthesis is extended while the DNA strand is released from the already-synthesized BIP primer by the activity of the Bst DNA Polymerase. (7) Double-strand DNA is formed by the above-described step (6). (8) On the other hand, since the DNA strand synthesized from the BIP primer released in step (6) has complementary sequences at both terminals, it self-anneals into a loop and forms a dumbbell-shaped structure. (9) Starting from the DNA strand having a dumbbell-shaped structure formed in step (8), the FIP primer and the subsequent BIP primer anneal, and the DNA amplification cycle proceeds.

The incubation time for the amplification operation may be 60 minutes, for example. During this incubation time, the DNA can be amplified by $10^9$ to $10^{10}$ fold by the annealing reaction and the DNA strand synthesis performed in the LAMP method.

Next, in the present embodiment, it is confirmed whether *Bursaphelenchus xylophilus* DNA is included in the reaction solution which underwent the amplification operation. More specifically, if *Bursaphelenchus xylophilus* is present in the pine specimen subjected to detection, the *Bursaphelenchus xylophilus* DNA will be amplified by the amplification operation, and detected. On the other hand, if *Bursaphelenchus xylophilus* is not in the pine specimen subjected to detection, *Bursaphelenchus xylophilus* DNA will not be amplified by the amplification operation, and thus not detected.

Whether amplified DNA is included in the reaction solution can be confirmed by fluorescence detection, for example. In the fluorescence detection, a fluorescence detection reagent is added to carry out the reaction, and the color of the reaction solution is visually confirmed. More specifically, if the reaction solution emits fluorescence, a positive determination can be made, namely, that *Bursaphelenchus xylophilus* DNA is amplified, while if the reaction solution does not emit fluorescence, a negative determination can be made, namely, that *Bursaphelenchus xylophilus* DNA is not amplified. The difference between positive and negative for reaction solution fluorescence can be more clearly determined by using a UV irradiation apparatus.

Although the present embodiment was described above, the present invention is not limited to the above description. The present invention may be applied in other embodiments. For example, the DNA amplification and detection method carried out in the LAMP method is not limited to fluorescence detection, and can be arbitrarily changed. Specifically, since the amplification reaction solution is cloudy due to the effects of the magnesium pyrophosphate produced as an amplification byproduct, *Bursaphelenchus xylophilus* DNA amplification may also be detected by measuring the turbidity of the amplification reaction solution at this stage. In addition, *Bursaphelenchus xylophilus* DNA amplification may also be detected using various nucleic acid amplification methods that are known regarding gene amplification, such as PCR (polymerase chain reaction).

In addition, the method for amplifying and detecting DNA by the LAMP method using the LAMP primer according to the present invention is not limited to cases in which *Bursaphelenchus xylophilus* DNA is directly extracted from a piece of wood. This method can also be applied in cases in which *Bursaphelenchus xylophilus* is isolated from a piece of wood by a method such as the Baermann method, and the DNA is then extracted.

EXAMPLES

The present invention will now be described in more detail based on the following examples. However, these examples in no way limit the present invention.

Example 1

The pine specimens used in the present example were collected from 10 dead Japanese black pines in the Forestry and Forest Products Research Institute's main research facility. Five of those trees were Japanese black pines (Japanese black pines killed by artificial inoculation of *Bursaphelenchus xylophilus*) infected with *Bursaphelenchus xylophilus*. The remaining 5 tress were Japanese black pines (Japanese black pines that were felled in a healthy condition and then isolated in a mesh area to prevent *Bursaphelenchus xylophilus* infection) that were not infected with *Bursaphelenchus xylophilus*.

*Bursaphelenchus xylophilus* DNA from the collected pine specimens was extracted, and a *Bursaphelenchus xylophilus* DNA extraction solution was prepared. Specifically, 1 ml of a DNA extraction buffer (100 mM NaCl, 10 mM tris-HCl (pH 8.0), 1 mM EDTA) was charged into a 1.5 ml microtube. Next, 40 µl of a DNA extraction kit (ISOHAIR, Nippon Gene Co., Ltd.), which included the keratinolytic enzyme Proteinase K, in a Lysis buffer and 50 pa of an enzyme solution were added to the DNA extraction buffer in the microtube, and the resultant mixture was thoroughly stirred. Next, about 0.06 g of the collected pine specimen was placed in the solution in the microtube, and incubated for 20 minutes at 55° C. and then for 10 minutes at 94° C.

Next, using the primer set according to the present invention and the above-described DNA extraction solution, amplification and detection operations were carried out by the LAMP method. Specifically, first, the primer set according to the present invention, the respective reagents of the Loopamp DNA amplification reagent kit (Eiken Chemical Co., Ltd.), and the Loopamp fluorescence detection reagent (Eiken Chemical Co., Ltd.) were dispensed into a 0.2 ml microtube in the below amounts to produce a reaction solution. The primer sets were obtained by the following method. An rDNA ITS region of *Bursaphelenchus xylophilus* and that of Bursaphelenchus mucronatus were amplified by the PCR method. The base sequence of those regions was determined using an ABI3100 DNA sequencer (Applied Biosystems). Then, the base sequence information for both species was analyzed using the LAMP primer design support software (Primer Explorer V4) provided on the web site of Eiken Chemical Co., Ltd. The LAMP primer was obtained by designing it so that only the *Bursaphelenchus xylophilus* DNA would be amplified.

2× Reaction Mix: 12.5 µl
Primer FIP (sequence ID No. 1): 1.0 µl (40 pmol/µl)
Primer BIP (sequence ID No. 2): 1.0 µl (40 pmol/µl)
Primer F3 (sequence ID No. 3): 1.0 µl (5 pmol/µl)
Primer B3 (sequence ID No. 4): 1.0 µl (5 pmol/µl)
Primer Loop-F (sequence ID No. 5): 1.0 µl (20 pmol/µl)
Bst DNA Polymerase: 1.0 µl
Fluorescence Detection Reagent: 1.0 µl
Distilled Water: 3.5 µl
Total: 23.0 µl Next, 2 µl of the above-described DNA extraction solution was added to the amplification reaction solution. The resultant mixture was thoroughly stirred, and then left for 1 hour at 63° C.

After 1 hour, it was visually confirmed whether the amplification reaction solution emitted green fluorescence. The results are shown in Table 1. Cases determined to be positive, in which green fluorescence was emitted, are marked with a circle (○), and cases determined to be negative, in which green fluorescence was not emitted, are marked with a cross (x).

TABLE 1

Detection results of *Bursaphelenchus xylophilus* based on the LAMP method using specimens taken from Japanese black pines that had died due to *Bursaphelenchus xylophilus* infection (nematode infection) and Japanese black pines killed by artificial felling (nematode non-infection).

| Condition of Dead Tree | Repetition 1 | 2 | 3 | 4 | 5 |
|---|---|---|---|---|---|
| Nematode Infection | ○ | ○ | ○ | ○ | ○ |
| Nematode Non-Infection | x | x | x | x | x |

Furthermore, detection was also carried out using the Baermann method for pine specimens collected from the same trees as each of the examples. The same detection results were obtained as those illustrated in the above Table 1. Accordingly, the effectiveness of the detection method of the present embodiment according to the present invention was shown.

Examples 2 and 3

Next, as Examples 2 and 3 of the present invention, the effectiveness of *Bursaphelenchus xylophilus* detection using DNA amplification based on the LAMP method and the PCR method was investigated.

First, a specimen was collected from a dead tree growing in a Forestry and Forest Products Research Institute facility. *Bursaphelenchus xylophilus* was isolated by applying the Baermann method on 8 g of the collected piece of wood. Next, the nematode concentration (number of *Bursaphelenchus xylophilus* per 1 g) in the collected specimen was calculated.

Furthermore, 8 samples for DNA extraction of about 0.06 g were prepared from the remaining specimen, and used for DNA extraction. Specifically, 1 ml of a DNA extraction buffer (100 mM NaCl, 10 mM tris-HCl (pH 8.0), 1 mM EDTA) was charged into a 1.5 ml microtube. Next, 40 μl of a DNA extraction kit (ISOHAIR, Nippon Gene Co., Ltd.), which included the keratinolytic enzyme Proteinase K, in a Lysis buffer and 50 μl of an enzyme solution was added to the DNA extraction buffer in the microtube, and the resultant mixture was thoroughly stirred. Next, about 0.06 g of each sample for DNA extraction was placed in the solution in the microtube, and incubated for 20 minutes at 55° C. and then for 10 minutes at 94° C.

Using these 8 DNA extraction solutions, detection was carried out by amplifying *Bursaphelenchus xylophilus* DNA by the LAMP method and the PCR method. The method and conditions for the detection carried out using the LAMP method are the same as described above in Example 1, and thus a description thereof is omitted here.

The detection carried out using the PCR method for Example 3 was performed as follows. First, GoTaq (Green Master Mix (Promega KK)) and a primer set for amplifying an rDNA ITS region of *Bursaphelenchus xylophilus* by the PCR method were dispensed into a 0.2 ml microtube to produce a reaction solution. The primer sequences forming the primer set were represented by sequence ID Nos. 6 and 7.

GoTaq Green Master Mix: 10.0 μl

Bx18S[1)] (sequence ID No. 6): 2.5 μl (2 pmol/μl)

Bx28S[1)] (sequence ID No. 7): 2.5 μl (2 pmol/μl)

Distilled Water: 3.0 μl

Total: 18.0 μl

[1)] Aikawa, T., Kikuchi, T. and Kosaka, H. (2003) Demonstration of interbreeding between virulent and avirulent populations of *Bursaphelenchus xylophilus* (Nematoda: Aphelenchoididae) by PCR-RFLP method. Appl. Entomol. Zool. 38: 565-569.

To this reaction solution, 2 μl of the above-described DNA extraction solution was added. *Bursaphelenchus xylophilus* DNA was then amplified by a PCR reaction using an iCycler thermal cycler (Bio-Rad Laboratories KK). The PCR conditions were set as follows. First, 35 cycles were carried out at 94° C./1 min.-53° C./1 min.-72° C./1 min., and cycling was finally carried out for 2 minutes at 72° C.

The 8 amplification reaction solutions were injected into agarose gel, subjected to electrophoresis, and then stained with ethidium bromide. Whether DNA was detected or not was determined by confirming the presence of DNA amplification by UV irradiation.

The application results of Examples 2 and 3 are shown below. First, as a result of nematode isolation by the Baermann method, the specimen subjected to detection according to the present embodiment was confirmed to have about 17 *Bursaphelenchus xylophilus* living therein per 1 g.

The detection results using the LAMP method and the PCR method are shown in Table 2.

TABLE 2

| DNA Amplification Method | Sample Number | Number of Successes Detected (amplification success number) | Number of Failures Detected (amplification failure number) | Detection Success Ratio (%) (amplification success ratio) |
|---|---|---|---|---|
| LAMP Method (Example 2) | 8 | 8 | 0 | 100 |
| PCR Method (Example 3) | 8 | 1 | 7 | 13 |

As shown in Table 2, in all of the 8 samples used in Example 2, *Bursaphelenchus xylophilus* DNA was amplified and detected. The results of Examples 2 and 3 show that in the *Bursaphelenchus xylophilus* detection method according to the present invention, in which DNA is extracted by causing a keratinolytic enzyme to act on a piece of wood, and the extracted DNA is amplified and detected, amplification and detection of a specific region of the rDNA of *Bursaphelenchus xylophilus* by the LAMP method using the above-described LAMP primer set is preferred.

Furthermore, from the results of Examples 2 and 3, it is clear that when the above-described LAMP primer set is used in amplification of *Bursaphelenchus xylophilus* DNA extracted by causing an enzyme which breaks down keratin to act on apiece of wood which includes *Bursaphelenchus xylophilus*, a much higher amplification success rate is exhibited than for other primers used in the PCR method.

The invention claimed is:

1. A method for extracting *Bursaphelenchus xylophilus* DNA from a piece of wood, comprising:

dipping a piece of wood including *Bursaphelenchus xylophilus* in a solution including an enzyme which breaks down keratin; and extracting a DNA of the *Bursaphelenchus xylophilus*.

2. A LAMP primer set, comprising the primers of sequence ID Nos. 1 to 4.

3. The LAMP primer set according to claim 2, further comprising a primer of a base sequence Loop-F represented by sequence ID No. 5.

4. A method for detecting *Bursaphelenchus xylophilus* DNA, characterized by comprising a step of amplifying a specific region in an rDNA of the *Bursaphelenchus xylophilus* using the LAMP primer set according to claim 2 by a LAMP method for detection.

5. A method for detecting *Bursaphelenchus xylophilus*, comprising:

a step of dipping a piece of wood including *Bursaphelenchus xylophilus* in a solution including an enzyme which breaks down keratin and extracting a DNA of the *Bursaphelenchus xylophilus*; and a step of amplifying and detecting the extracted *Bursaphelenchus xylophilus* DNA.

6. The method for detecting *Bursaphelenchus xylophilus* according to claim 5, wherein the step of amplifying and detecting *Bursaphelenchus xylophilus* DNA is carried out by amplifying and detecting a specific region of an rDNA of the *Bursaphelenchus xylophilus* by a LAMP method using a first LAMP primer set comprising primers of respective base sequences F3, B3, FIP, and BIP, which are represented by sequence ID Nos. 1 to 4 or a second LAMP primer set comprising primers for respective base sequences F3, B3, FIP, BIP, and Loop-F which are represented by sequence ID Nos. 1 to 5.

* * * * *

SEQUENCE LISTING

<160> NUMBER OF SEQ ID NOS: 7

<210> SEQ ID NO 1
<211> LENGTH: 18
<212> TYPE: DNA
<213> ORGANISM: Artificial sequence
<220> FEATURE:
<223> OTHER INFORMATION: Synthetic construct; Bursaphelenchus xylophilus (F3 primer)

<400> SEQUENCE: 1
gcagaaacgc cgacttgt 18

<210> SEQ ID NO 2
<211> LENGTH: 19
<212> TYPE: DNA
<213> ORGANISM: Artificial sequence
<220> FEATURE:
<223> OTHER INFORMATION: Synthetic construct; Bursaphelenchus xylophilus (B3 primer)

<400> SEQUENCE: 2
tcatccgaac gtccctgac 19

<210> SEQ ID NO 3
<211> LENGTH: 41
<212> TYPE: DNA
<213> ORGANISM: Artificial sequence
<220> FEATURE:
<223> OTHER INFORMATION: Synthetic construct; Bursaphelenchus xylophilus (FIP primer)

<400> SEQUENCE: 3
cgcggaacaa accgcgtaaa accgttgtga cagtcgtctc g 41

<210> SEQ ID NO 4
<211> LENGTH: 41
<212> TYPE: DNA
<213> ORGANISM: Artificial sequence
<220> FEATURE:
<223> OTHER INFORMATION: Synthetic construct; Bursaphelenchus xylophilus (BIP primer)

<400> SEQUENCE: 4
agagggcttc gtgctcgatt ggccgttgaa acaacatcac c 41

<210> SEQ ID NO 5
<211> LENGTH: 20
<212> TYPE: DNA
<213> ORGANISM: Artificial sequence
<220> FEATURE:
<223> OTHER INFORMATION: Synthetic construct; Bursaphelenchus xylophilus (LoopF primer)

<400> SEQUENCE: 5
agatggtgcc taacattgcg 20

<210> SEQ ID NO 6
<211> LENGTH: 20
<212> TYPE: DNA
<213> ORGANISM: Artificial sequence
<220> FEATURE:
<223> OTHER INFORMATION: Synthetic construct; Bursaphelenchus xylophilus (PCR primer, Bx18S)

-continued

```
<400> SEQUENCE: 6

aaactaggga tcgctggagt                                                   20


<210> SEQ ID NO 7
<211> LENGTH: 20
<212> TYPE: DNA
<213> ORGANISM: Artificial sequence
<220> FEATURE:
<223> OTHER INFORMATION: Synthetic construct; Bursaphelenchus xylophilus
      (PCR primer, Bx28S)

<400> SEQUENCE: 7

ttcagcaggt agtcataccc                                                   20
```